United States Patent
Fatiny

(10) Patent No.: US 9,636,194 B2
(45) Date of Patent: May 2, 2017

(54) DENTAL DEVICE WITH DUAL SALIVA EXTRACTION AND DUAL RETRACTOR

(71) Applicant: King Saud University, Riyadh (SA)

(72) Inventor: Fahad Ibrahim Fatiny, Riyadh (SA)

(73) Assignee: King Saud University, Riyadh (SA)

( * ) Notice: Subject to any disclaimer, the term of this patent is extended or adjusted under 35 U.S.C. 154(b) by 106 days.

(21) Appl. No.: 14/274,802

(22) Filed: May 12, 2014

(65) Prior Publication Data

US 2015/0320527 A1    Nov. 12, 2015

(51) Int. Cl.
*A61C 17/10* (2006.01)
*A61C 17/06* (2006.01)
*A61B 13/00* (2006.01)

(52) U.S. Cl.
CPC ........... *A61C 17/043* (2013.01); *A61B 13/00* (2013.01)

(58) Field of Classification Search
CPC ......... A61C 17/04; A61C 17/043; A61C 5/14; A61B 1/06; A61B 1/24
USPC ...................................................... 433/91–96
See application file for complete search history.

(56) References Cited

U.S. PATENT DOCUMENTS

| | | | | |
|---|---|---|---|---|
| 1,401,646 A * | 12/1921 | Ronn | .................... | A61C 17/043 433/140 |
| 2,519,595 A * | 8/1950 | Older | .................... | A61C 17/043 138/118 |
| 2,587,008 A | 10/1950 | Stadelmann | | |
| 2,859,519 A * | 11/1958 | Cohn | .................... | A61C 17/043 433/93 |
| 3,078,578 A * | 2/1963 | White | .................. | A61C 17/043 433/136 |
| 3,256,885 A * | 6/1966 | Higgins | ................ | A61C 17/043 433/91 |
| 3,396,468 A * | 8/1968 | Dayhoff | ................. | A61C 5/122 433/140 |
| 3,426,430 A * | 2/1969 | Newman | .............. | A61C 17/043 433/96 |
| 3,455,024 A * | 7/1969 | Gelarie | ................ | A61C 17/043 433/93 |
| 3,916,880 A * | 11/1975 | Schroer | ..................... | A61B 1/24 600/205 |
| 4,019,255 A * | 4/1977 | Cohen | .................. | A61C 17/043 433/93 |

(Continued)

FOREIGN PATENT DOCUMENTS

| | | | | |
|---|---|---|---|---|
| DE | 19942256 A1 * | 3/2001 | ............... | A61C 5/14 |
| FR | 1108049 A * | 1/1956 | ........... | A61C 17/043 |

(Continued)

*Primary Examiner* — Cris L Rodriguez
*Assistant Examiner* — Matthew Saunders
(74) *Attorney, Agent, or Firm* — Hauptman Ham, LLP

(57) ABSTRACT

A dental device with dual saliva extractors and dual retractors for the tongue and upper lip and method are connectable to a suction and disposal unit. The device includes a pair of extractors each of which includes a suction tip and a tubular member for connecting the tip to the sources of suction. A first of the tubular members is put into a patient's mouth with a first curved portion inserted in a lower portion of the patient's mouth over the tongue and behind the front teeth and a second curved portion separate from said first portion branched off from where the first portion crosses the lower teeth and is inserted between the upper lip and upper molars under the region of the Stenson's duct.

1 Claim, 2 Drawing Sheets

(56) References Cited

U.S. PATENT DOCUMENTS

| | | | | |
|---|---|---|---|---|
| 4,053,984 A | * | 10/1977 | Moss | A61C 17/043 |
| | | | | 433/140 |
| 4,215,984 A | | 8/1980 | Reichley | |
| 4,259,067 A | * | 3/1981 | Nelson | A61C 17/043 |
| | | | | 433/138 |
| 4,260,378 A | * | 4/1981 | O'Neil | A61C 17/043 |
| | | | | 433/93 |
| 5,071,347 A | | 12/1991 | McGuire | |
| 5,890,899 A | | 4/1999 | Sclafani | |
| 2003/0054317 A1 | * | 3/2003 | Burney | A61C 17/043 |
| | | | | 433/96 |
| 2012/0237894 A1 | * | 9/2012 | Maycher | A61C 17/043 |
| | | | | 433/95 |
| 2013/0095450 A1 | * | 4/2013 | Ames | A61C 17/043 |
| | | | | 433/93 |

FOREIGN PATENT DOCUMENTS

| | | | | | |
|---|---|---|---|---|---|
| GB | | 973868 A | * | 10/1964 | A61C 17/043 |
| JP | WO 9937238 A1 | | * | 7/1999 | A61C 17/043 |

\* cited by examiner

DENTAL DEVICE WITH DUAL SALIVA EXTRACTION AND DUAL RETRACTOR

FIELD OF THE INVENTION

This invention relates to dental device with dual saliva extractors and dual retractors for the tongue and an upper lip adjacent a row of molars.

BACKGROUND OF THE INVENTION

When performing various procedures with the oral cavity, it is often desirable, if not necessary, for the dental practitioner to slow or divert the flow of saliva produced by the salivary glands. There are four principle salivary glands within the oral cavity. The two parotid salivary glands are located inside the mouth and near each ear. There are also two sublingual salivary glands located near the base of the tongue. The vast majority of saliva produced enters a patient's mouth through these principle salivary glands. A minor amount also enters through the mucosals. Several devices and techniques have been employed in order to prevent the saliva from interfering with the dental practitioner's work inside the oral cavity.

Rolls of cotton have been used in an attempt to prevent saliva produced by the principle salivary glands from interfering with the work of a dental practitioner within the oral cavity. The cotton roll is placed below the salivary gland. As saliva is produced it drains downward, and is absorbed by the cotton. One disadvantage of using cotton rolls is that they are rather large and restrict the ability of the dental practitioner to work within the oral cavity because they take up so much space. In addition, they quickly saturate necessitating removal and replacement of the cotton during the procedure. It is often difficult to maintain the cotton roll in the position place. Finally, cotton rolls can be uncomfortable for the patient.

Rubber dams have been used for isolating an area of the mouth from saliva. Rubber dams are difficult to use as they must be assembled which can take a significant amount of time. In addition, when using a rubber dam, the patient cannot completely close his or her mouth. This makes it difficult for the dental practitioner to check the patient's occlusion, and is generally uncomfortable for the patient.

Dental suction tubes have also been used to remove access saliva produced by the salivary glands. Generally the suction tube is inserted periodically to remove excess saliva as it pools in the patient's mouth. This either requires an assistant to periodically insert the suction tube, or it requires interrupting the dental practitioner's work.

An early U.S. patent of Stadelmann U.S. Pat. No. 2,587,008 discloses a dental appliance that includes a sublingual suction fork with tongue depressor. The sublingual suction fork with tongue depressor are disposed inward of the lower teeth while an upper suction fork is disposed outwardly of the lower teeth to receive saliva from the parotid glands.

A more recent U.S. patent of McGuire U.S. Pat. No. 5,071,347 discloses a distal instrument for removing saliva. The McGuire instrument includes a pair of tubes positioned within a patient's mouth to support a pair of absorbent rolls on the sides of the alveolar ridge. One of the tubes terminates at its proximal end in a suction adaptor for contact interface with a suction tube connected to a dental suction device. The proximal end of the other of the tubes intersects the first tube at its mid-length. An absorbent roll supporting a perforated stem is removably inserted into the distal end of each of the tubes. Each stem includes a number of apertures in fluid communication with the passageways through the pair of tubes so that suction applied at the suction adapter operates through the apertures to remove fluid absorbed by the absorbent rolls.

Notwithstanding the above, it is presently believed that there is a need and a potential commercial market for an improved dual saliva extractor and dual retractor for removing saliva and restricting movement of the tongue and upper lip near one of the Stenson's ducts.

SUMMARY OF THE INVENTION

In essence, the present invention contemplates a disposable dental device with dual saliva extractors and dual retractors for the tongue and an upper lip near one of the Stenson's ducts. The device is adapted to be connected to a dental operatory i.e., a dental suction and disposable unit for extraction and disposal of saliva, small amounts of blood and water and debris.

The device comprises or consists of a first and a second saliva extractor each of which includes a suction tip and a tubular member connecting the suction tips to the dental suction and disposal unit for removing liquids, saliva etc. from a patient's oral cavity.

In a preferred embodiment of the invention a first of said tubular members includes a semi rigid curved portion made of a semi rigid thermoplastic and is inserted in a lower portion of the patient's mouth over the tongue and behind the front teeth. A second semi rigid tubular member made of a semi rigid plastic is branched off from the curved portion of the first tubular member where it crosses over the lower teeth. The second suction tip of the second tubular member is then inserted between an upper lip and the upper teeth or molars in the region of one of the Stenson's ducts.

A second embodiment of the invention relates to a method for removing saliva and other liquid and debris from a patient's mouth during dental procedures. The method comprises or consists of the following steps.

The first step in the method calls for providing a dental device having a dual saliva extractor and dual retractor for the tongue and upper lips. The device is connected to a source of dental suction and a liquid disposal for removal of saliva, other liquids and debris from a patient's mouth. A first and a second of the dual saliva extractors each of which includes a suction tip and a semi rigid tubular member connecting each of the suction tips to a source of dental suction and disposal and wherein a first of the tubular members includes a curved portion.

The device is inserted in the mouth of a patient with the curved portion of the first tubular member extending across the lower teeth of the patient and a first suction tip in a sublingual portion of the patient's mouth.

The method also includes the step of inserting the second suction tip with the second tubular member attached thereto under the patient's upper lip between the patient's cheek and molars with the second suction tip under one of the Stenson's ducts.

The method further includes the step of subjecting the saliva extractors to the source of suction, performing a dental procedure; and removing the dental device from the patient's mouth.

The invention will now be described in connection with the accompanying drawings wherein like reference numerals have been used to identify like parts.

DETAILED DESCRIPTION OF THE PREFERRED EMBODIMENT OF THE INVENTION

Figure 1:
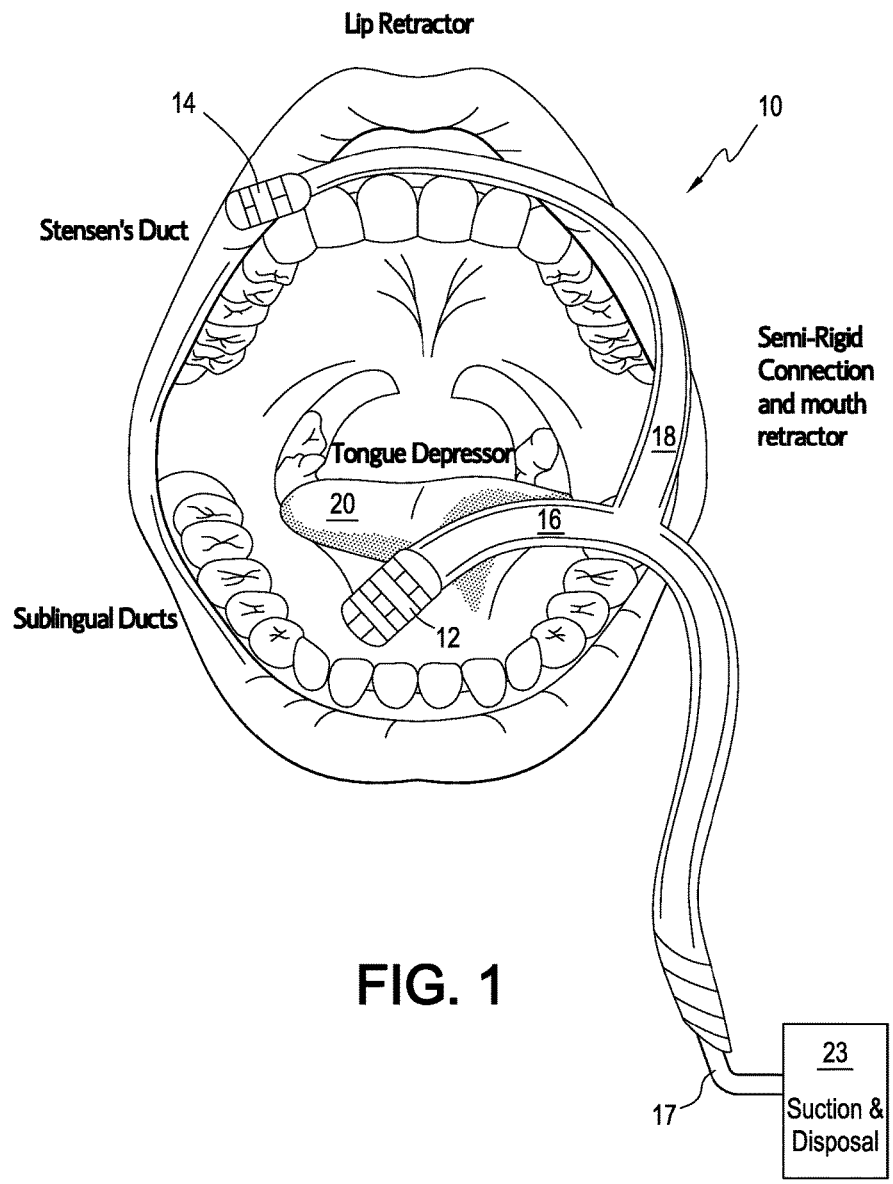
FIG. 1 is a schematic illustration of a dental device superimposed on an opened mouth of a patient.

As illustrated in FIG. 1, a dental device 10 comprises and/or consists of a pair of saliva extractors 12 and 14, a first saliva extractor 12 for removing liquid from the sublingual portion of the oral cavity and a second saliva extractor 14 between a patient's cheek and upper teeth below one of the patient's Stenson's duct. The saliva extractors 12 and 14 are each connected to a semi rigid tubular member 16 and 18, respectively.

A tongue depressor 20 is attached at one end of a first tubular member 16 near the first saliva extractor. In one embodiment of the invention the tubular member 16 extends across the patient's tongue and acts as a dental retractor to prevent the tongue from contacting a dental workplace. In a preferred embodiment of the invention, the depressor 20 serves as a retractor and depresses the tongue to remove the tongue from the workplace.

The first tubular member 16 is adapted to be connected at its distal end 17 to a source of suction and disposal such as a dental operatory for extracting saliva and debris from a lower part of the patient's mouth. As illustrated, the first tubular member 16 includes a curved portion 19 inserted into a lower portion of the mouth behind the front teeth and over the tongue. A second tubular member 18 also includes a curved portion 21 and includes a distal end 17 wherein the second tubular member is operatively connected to the first tubular member and is thus also connected by way of the first tubular member to a source of dental suction 23. The curved portion 21 extends upwardly in a patient's mouth so that the second saliva extractor and a forward part of the second tubular member 18 can be placed between the upper lip and the upper molars with the saliva extractor 14 below a Stenson's duct.

In a preferred embodiment of the invention, the tubular members 16 and 18 are made of a semi rigid thermoplastic material as for example polyethylene, polypropylene and polyterpene and or the like.

Figure 2:
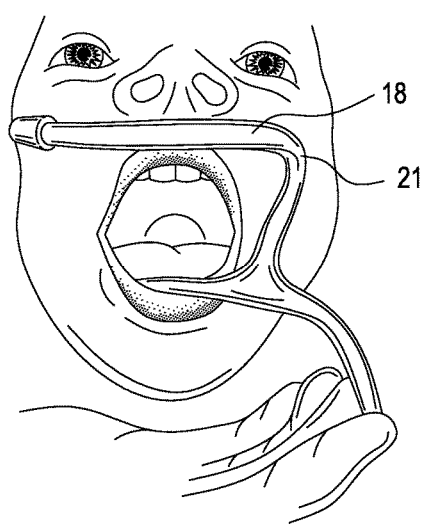
FIG. 2 is a schematic illustration of a first tubular member between a patient's lower lip and the lower teeth.

FIGS. 2-5 include the steps of installing a device in accordance with the present invention in a patient's oral cavity. For example, FIG. 2 illustrates a first step wherein a first saliva extractor 12 is inserted into a patient's mouth with a first tubular member 16 across the tongue and the extractor 12 is in a lower portion of the oral cavity underneath the patient's tongue.

Figure 3:
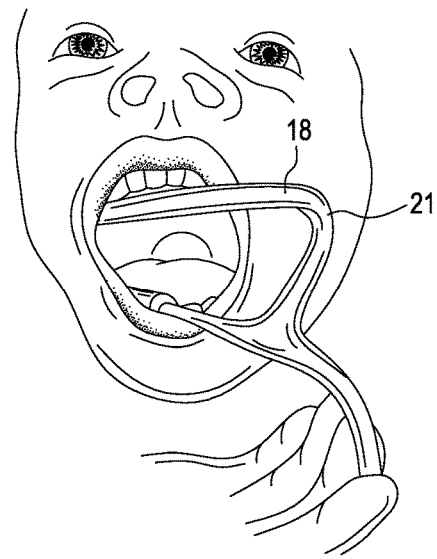
FIG. 3 is a schematic illustration of a second suction tip under an upper lip of a patient.

With respect to FIG. 3, the second saliva extractor 14 is inserted under the upper lip with the second tubular member 18 extending across the upper front teeth before the tip of the second extractor 12 is pushed back along the outside of the upper molars to a position beneath one of the Stenson's ducts.

Figure 4:
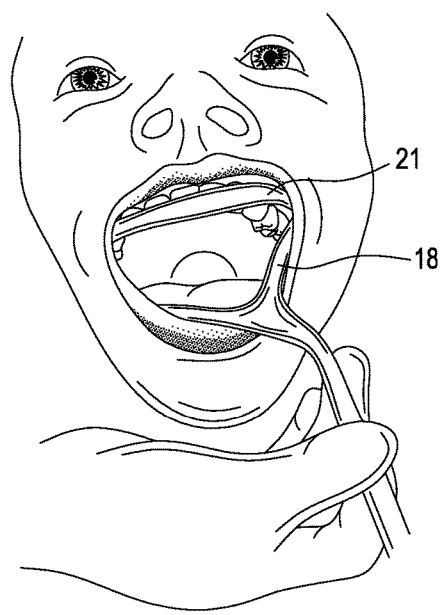
FIG. 4 is a schematic illustration of the retractor's loop over a patient's tongue.
Figure 5:
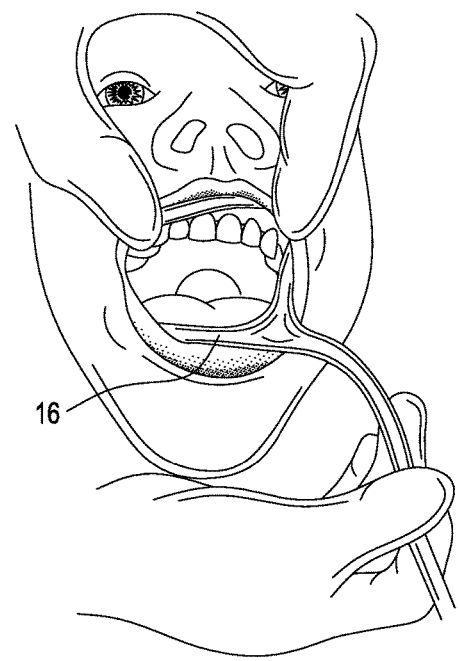
FIG. 5 is a schematic view of the dental device as installed in a patient's mouth.

FIG. 4 illustrates the dental device 10 in a patient's mouth with the second tubular member 18 across a patient's upper front teeth. In FIG. 5, the second tubular member has been pushed up under the upper lip which tends to hold the second (curved) portion of the saliva extractor under one of the Stenson's ducts in a patient's mouth.

While the invention has been described in connection with its preferred embodiments, it should be recognized that changes and modifications may be made therein without departing from the scope of the appended claims.

What is claimed is:

1. A method for removing saliva and other liquids and debris from a patient's mouth during a dental procedure, said method consisting of:
    providing a dental device having a dental suction and disposal unit, a first semi-rigid tubular member and a second semi-rigid tubular member branched off from said first semi-rigid tubular member and made from a thermoplastic material selected from the group consisting of polyethylene, polypropylene and polyterpene that act as a pair of retractors for the tongue and upper lip; and
    a pair of saliva extractors and wherein each of said saliva extractors include a suction tip connected to said dental suction and disposal unit by one of said semi-rigid tubular members; and
    wherein each of said tubular members includes a curved portion;
    a tongue depressor attached to said first tubular member between said suction tip and said saliva extractor and said second tubular member where it is branched out from said first tubular member and wherein said tongue depressor covers a portion of the tongue;
    providing said dental device having a dental suction and disposal unit, a pair of semi-rigid tubular members that act as a pair of retractors for the tongue and upper lip; connecting said device to a source of suction and a liquid disposal unit for removal of saliva, other liquids and debris from a patient's mouth; a first and a second of the dual saliva extractors each of which includes one of said suction tips and a semi-rigid tubular member connecting each of the suction tips to said source of suction and disposal unit and wherein a first of said tubular members includes a curved portion;
    inserting the device in the mouth of a patient with the curved portion of the first tubular member extending across the lower teeth of the patient and a first suction tip in a sublingual portion of a patient's mouth;
    inserting the second suction tip with the second tubular member attached thereto under the patient's upper lip between the patient's cheek and molars with the second suction tip under one of the Stenson's ducts;
    subjecting the saliva extractor to a source of suction;
    performing a dental procedure; and
    removing the dental device from the patient's mouth.

* * * * *